United States Patent [19]
Stern et al.

[11] Patent Number: 6,147,196
[45] Date of Patent: Nov. 14, 2000

[54] PROCESS FOR PRODUCING ESTERS OF FATTY SUBSTANCES AND THE HIGH PURITY ESTERS PRODUCED

[75] Inventors: Robert Stern, Conflans Sainte Honorine; Gérard Hillion, Herblay; Jean-Jacques Rouxel, Longuesse, all of France

[73] Assignee: Institut Francais du Petrole, Rueil Malmaison Cedex, France

[21] Appl. No.: 09/213,286

[22] Filed: Dec. 17, 1998

[30] Foreign Application Priority Data

Dec. 18, 1997 [FR] France ................................ 97 16293

[51] Int. Cl.⁷ .......................................................... C11C 1/00
[52] U.S. Cl. ............................................. 534/170; 584/169
[58] Field of Search ...................................... 554/169, 170

[56] References Cited

FOREIGN PATENT DOCUMENTS

| 391485 | 10/1990 | European Pat. Off. . |
| 2752242 | 2/1998 | France . |
| 795573 | 5/1958 | United Kingdom . |

*Primary Examiner*—Deborah D. Carr
*Attorney, Agent, or Firm*—Millen, White, Zelano & Branigan, P.C.

[57] ABSTRACT

In order to produce a composition of esters of linear mono-carboxylic acids containing 6 to 26 carbon atoms and glycerine simultaneously with high degrees of purity, the following is carried out:

a step a) in which a plant or animal oil, which may or may not be acidic, is reacted with an excess of at least one aliphatic mono-alcohol containing 1 to 4 carbon atoms in the presence of a heterogeneous catalyst, eliminating the excess mono-alcohol and separating out glycerine, this step producing a crude ester containing residual mono-glycerides;

a step b) in which the crude ester obtained undergoes transesterification or esterification of the residual mono-glycerides to di- and tri-glycerides, in the presence of a heterogeneous catalyst; and a step c) in which the ester composition is evaporated under reduced pressure, recycling the evaporation residue to the starting oil of step a). The ester compositions obtained, which are of high purity, are of particular use as gas oil substitutes.

16 Claims, No Drawings

PROCESS FOR PRODUCING ESTERS OF FATTY SUBSTANCES AND THE HIGH PURITY ESTERS PRODUCED

FIELD OF THE INVENTION

The present invention relates to a novel process for producing particularly pure esters of fatty substances, the process being carried out in three principal steps: a first step, in which a plant or animal oil is reacted with a mono-functional alcohol in the presence of a heterogeneous catalyst to form a fatty acid ester of that alcohol; then the reaction is completed by evaporating off the excess alcohol used and separating out the glycerine formed by settling, for example; a second step, in which the mono-glycerides present in the crude ester obtained in the first step are reacted in the presence of a heterogeneous catalyst with the ester of the mono-alcohol which is formed, to transform them into heavier products such as di-glycerides and tri-glycerides; and a third step, in which the crude, not cooled ester from the second step is evaporated, the residue being recycled to the first step.

BACKGROUND OF THE INVENTION

Esters of mono-alcohols derived from plant or animal oils have numerous applications. The main application to be pointed out is that of substitute fuels for gas oil in which the usual oils can be used as starting materials, such as rapeseed oil and sunflower seed oil, and also oils containing a high proportion of saturated fatty acids linked to glycerine, such as palm oil or tallow, to produce high purity esters. However, in that application, the presence of even trace amounts of saturated mono-glycerides of fatty acids is particularly deleterious, as mono-glycerides tend to crystallise over time and thus block filters.

In this regard, the invention proposes a process which can produce esters with a much reduced mono-glyceride content, and which also has the advantage of enabling a very pure glycerine to be produced which can be directly used in industrial or food applications without distillation.

When using esters as substitute gas oil fuels, it is also desirable to be able to use used cooking oil as the starting materials which initially contain both heavy products (dimers, trimers) and free fatty acids. The process of the invention can produce very pure esters from such starting materials.

Other applications have also been researched, such as those concerning the production of ester bases which, by ester hydrogenolysis, can produce alcohols or dimers or amides by dimerisation or amidation.

Methyl esters can be produced by conventional homogeneous catalysis techniques using soluble catalysts, such as sodium hydroxide or sodium methylate, by reacting a neutral oil and an alcohol such as methanol (JAOCS 61, 343–348, 1984).

Two main processes have been industrialised.

The first process consists of working under conditions which converts oil to methyl esters in very high yields. It is not necessary to evaporate the ester to eliminate the secondary products formed, especially when dealing with an unsaturated ester, in which the majority of fatty acids linked to the alcohol are unsaturated, i.e., oleic or linoleic acid type. In this case, traces of mono-glycerides which are present remain soluble in the ester.

A second process consists of evaporating off or distilling the ester at the end of the first transesterification step. To prevent the mono-glycerides present in the ester from being entrained, they are transformed into di- and/or tri-glycerides by reacting the mixture of esters obtained, free of alcohol or glycerine, at a temperature of 200° C. or more in the presence of a soluble basic catalyst. Under these conditions, soaps form with the alkaline catalyst, such that only a portion of the distillation or evaporation residue can be recycled, since partial elimination is necessary in order no to accumulate alkaline derivatives and heavy derivatives (esters of sterols present in proportions which vary depending on the nature of the oil).

It should be added that, in order to purify the glycerine, the two processes necessitate multiple steps, as the glycerine is polluted by alkaline salts or alcoholates, and the glycerine purification apparatus is almost as expensive as that for producing the ester.

Processes using heterogeneous catalysis employing a fixed bed have been described in the literature, in different patent documents (European patent EP-B-0 198 243, British patent GB-A-0 795 573, EP-B-0 198 243 and French patent FR-A-2 752 242).

Such processes have the advantage of producing esters and glycerine which are free of catalyst and are thus easy to purify. However, it has been shown that to obtain complete conversion of an oil to the ester, two steps generally have to be carried out which include a plurality of operations; thus, after the first transesterification step, the excess alcohol has to be evaporated off, the glycerine formed has to be eliminated, then alcohol has to be re-injected with the partially converted ester, the mixture is heated again and, after reacting, the alcohol is again evaporated off and the glycerine is settled out. To obtain complete conversion of the oil to the ester in one step, a very large excess of alcohol would be required along with a very long residence time (very low HSV). If all of the operations described above are not to be carried out, it appears to be preferable to distil or evaporate the ester after the first transesterification step. The crude ester can be distilled but this necessitates heavy investment in a plate column with the known risk of overheating the bottom of the column and a large energy consumption mainly due to an unavoidable reflux.

If evaporation or flash evaporation using a falling-film evaporator is used, there is a risk of entraining traces of mono-glycerides in the ester with a boiling point which is close to that of the ester, in particular when in the presence of esters with $C_{18}$ acids and mono-glycerides of $C_{16}$ acids which is the case when starting from certain oils which are rich in palmitic acid.

It is difficult to introduce alkaline products which can transform the mono-glycerides into heavier products into the ester, as is the case with homogeneous catalysis, since the alkaline products will pollute the heterogeneous catalyst and even the products produced such as glycerine.

SUMMARY OF THE INVENTION

It has now been discovered that, surprisingly, these disadvantages can be completely overcome by conducting, after the first step of transesterifying of plant or animal oil with a heterogeneous catalyst, a second step of transesterifying or esterifying the monoglycerides with the fatty acid esters present and/or, respectively, by adding at least one fatty acid containing 6 to 26 carbon atoms, using a heterogeneous catalyst which can be of the same nature as that used in the first step, before evaporating off the ester.

This second step, carried out with a heterogeneous catalyst and which is practically the reverse of the initial transesterification reaction, enables the evaporation residue can be recycled without loss, does not pollute the principal heterogeneous catalyst, and it means that evaporation can be carried out using a falling-film evaporator or any other non refluxed distillation technique, and a pure ester and a pure glycerine can be produced, this latter being produced in the first step.

Thus the invention provides a process for simultaneously producing high purity esters and glycerine using a process employing a heterogeneous catalyst and comprising three principal steps, the first, which is known, consisting of reacting an alcohol and an oil, the second, after eliminating excess alcohol and the glycerine formed, of reacting the mono-glycerides present in the ester obtained with the same ester to carry out the reaction below:

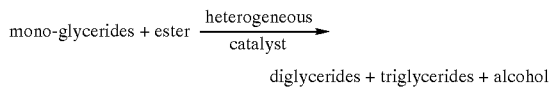

and the third step consisting of evaporating the ester which no longer contains mono-glyceride, this step naturally following the second step, without the necessity of cooling the ester obtained therein.

Thus in general, the invention provides a process for simultaneously producing a composition of esters of linear monocarboxylic acids containing 6 to 26 carbon atoms and glycerine with a high degree of purity, characterized in that it comprises:

a step a) in which a plant or animal oil, which may or may not be acidic, is reacted with an excess of at least one aliphatic mono-alcohol containing 1 to 4 carbon atoms in the presence of a heterogeneous catalyst, eliminating the excess alcohol and separating out the glycerine, this step producing a crude ester containing residual monoglycerides;

a step b) in which the crude ester obtained undergoes re-esterification of the residual monoglycerides to di- and tri-glycerides, in the presence of a heterogeneous catalyst; and a step c) in which the ester composition is evaporated off under reduced pressure, recycling the evaporation residue to the starting oil of step a).

The process of the invention can be applied to all oils the esters of which are easy to evaporate. Particularly suitable oils are saturated or unsaturated plant oils, such as soya oil, rapeseed oil, sunflower seed oil, linseed oil, peanut oil, coprah oil, palm nut oil, palm oil, safflower oil, linola oil and cottonseed oil, animal oils such as tallow, suet and fish oils, or used cooking oil. All of these oils can be acidic, but phospholipids will preferably have been eliminated from them before use, for example using a known process using phosphoric acid or citric acid.

DETAILED DESCRIPTION OF THE INVENTION

The particular conditions used in each of the steps of the process of the invention will now be described.

When starting from a neutral oil and depending on the the alcohol used, the reaction of step a) is generally carried out at a temperature in the range 180° C. to 250° C., preferably 180° C. to 200° C., at a pressure of 20 to 100 bars and an HSV (flow rate expressed as the volume of oil/volume of catalyst/hour) of 0.3 to 3. Under these conditions, 85% to 97% by weight of esters is generally obtained. In step a), it is important to operate under conditions for which the highest conversion is obtained, since step b) generally reduces the amount of ester by 2% to 8%.

There are many heterogeneous catalysts which can be used to carry out the principal reaction (step a))—and the second reaction (step b)). Examples are catalysts based on zinc, tin or titanium, for example aluminates or silicates, preferably aluminates. The catalyst is generally used in a proportion of 2% to 5% by weight with respect to the oil. It is preferable to use the same type of catalyst for the principal reaction (step a)) and for the second reaction (step b)).

Preferred alcohols for transesterification are conventional known alcohols (methanols, isopropanol, n-butanol, secondary butanol, isobutanol), but preferably methanol is used if gas oil substitutes are to be produced. In the latter case, the temperature is preferably 220° C. to 250° C. and the pressure is 40 to 100 bars, more particularly 30 to 60 bars. Further, a methanol/oil ratio of 1/3 to 2/1 is used.

The reactor used to carry out step a) can be fairly short. To increase the residence time and the rate of circulation of the reactants (oil+alcohol) over the catalyst, a certain fraction of the reaction volume leaving the reactor can be recovered while the other fraction is sent, for example, to a settler-evaporator, at the height of the volume of the mixture (oil+alcohol) which continuously supplies the reactor. Fixed bed and single pass techniques can also be used. After reacting, the excess alcohol (for example methanol) is evaporated partially due to a depressurisation to atmospheric pressure and, for traces of alcohol, by nitrogen stripping. After condensing, the alcohol recovered is dry and can be recycled without the need to purify it or rectify it, provided that the oil used at the start is neutral and dry.

The glycerine formed in step a) is generally separated by settling at a temperature of 20° C. to 100° C.

The glycerine produced is very pure and generally only slightly coloured. If necessary, it can be purified again (decolourised and/or deodorised) using conventional purification techniques, such as passage over charcoal, over activated clay or over a mixture of activated charcoal and activated clay.

In step b), the crude ester obtained in step a) can be introduced continuously either into a small fixed bed column containing the catalyst, or into a single reactor. In both cases, the alcohol formed, for example methanol, is eliminated continuously or discontinuously. The reaction temperature is 180° C. to 250° C. The time depends on the quantity of catalyst. With 2% to 5% by weight of catalyst with respect to the oil, a mono-glyceride content of less than 0.2%, or even less than 0.1% can be obtained in a short time.

Preferred temperatures for step a) and/or step b) are 180° C. to 200° C., to avoid the formation of ethers of glycerol as much as possible.

Further, to avoid losing the ester, before the reaction of step b), a quantity of free fatty acids which will preferentially react with the mono-glycerides at lower temperatures can be introduced. In general, an equal weight of $C_{18}$ fatty acids with respect to the mono-glycerides can be introduced. Esterification is particularly rapid with zinc aluminate catalysts. Thus, fatty acids from refining acidic oils can be used, for example. However, these fatty acids must not contain alkaline ions or phospholipids. Thus the ester yield with respect to the oil used can be increased using another route. The other interest in reacting fatty acids is that, instead of producing alcohol, water is evaporated.

Thus the following properly controlled reaction occurs, at a temperature at which only the fatty acid reacts:

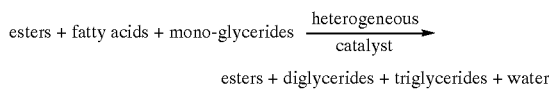

$$\text{esters + fatty acids + mono-glycerides} \xrightarrow[\text{catalyst}]{\text{heterogeneous}}$$
$$\text{esters + diglycerides + triglycerides + water}$$

In step c), the ester, which contains little or no monoglycerides, is injected, for example, into a falling-film evaporator. The purity of the ester, if only the presence of the mono-, di- and tri-glycerides and sterol esters are considered, can reach at least 99%. The vacuum required for this evaporation is generally less than 3 mm of mercury with $C_{18}$ esters. The ester is generally condensed then stored and stabilised using an antioxidant.

If the starting oil is acidic, for example with an acid number of 10, two techniques can be used.

The first technique consists of using the acidic oil directly, which must, however, be free of phospholipids. In this case, oil conversion is good, as fatty acids generally react better than tri-glycerides. However, water forms which hydrates the alcohol (for example methanol). The quantity of glycerine formed does not appear to be sufficient to dry this alcohol. Further, this would require fairly controlled distillation of the alcohol (for example methanol) hence the requirement to operate with a certain reflux ratio.

If the alcohol is hydrated and if the latter is recycled a number of times, an ester is eventually formed which is more or less rich in fatty acidity from hydrolysis of the methyl ester. In order to avoid this problem, which eventually risks accumulating water in the alcohol (methanol) if hydrolysis is incomplete, the second technique is used which consists, before using the oil, of reducing the amount of fatty acid by reacting it with small quantities of glycerine in the presence of a heterogeneous catalyst, which may be the same catalyst as that used in the first step, or a similar heterogeneous catalyst.

As is known, an oil is obtained which is slightly or not acidic under good conditions of 180° C. to 200° C., at atmospheric pressure or a slight vacuum or by nitrogen entrainment.

In the above two techniques, where the acidic oil is esterified either with a mono-alcohol or with glycerine, it is preferable to use a heterogeneous catalyst as defined above but which only forms a salt with a fatty acid under the reaction conditions with difficulty.

In the process of the invention, for the principal reaction with the mono-alcohol (step a)), it is important to use a fixed bed column as the pressure is relatively high, for example up to about 60 to 100 bars. For the reaction of acid oils with glycerine, in which water is eliminated, and for transesterification of mono-glycerides (step b)), in which alcohol is eliminated, single batch reactors can be used as the operating pressures are close to or below atmospheric pressure.

In contrast to the case of residues obtained from homogeneous catalysis, recycling the evaporation residues does not pose any problems as this residue does not contain any new product. A portion of the sterols in the form of esters of sterols, and the di- and tri-glycerides, are present in the residue. However, when the residue added to he oil is subjected to the action of excess alcohol (in particular methanol), the above products re-transform into sterols, alkyl esters (in particular methyl) and glycerine.

The entire disclosure of all applications, patents and publications, cited above and below, and of corresponding French application 97/16293, filed Dec. 18, 1997, are hereby incorporated by reference.

Some non limiting examples will now be given.

EXAMPLE 1

Step 1:

A neutral rapeseed oil (neutralised and bleached) was passed at a rate of 70 cm³/hour with methyl alcohol at the same rate through a 0.47 m long, 2.7 cm diameter tube reactor from bottom to top, heated to 230° C. by three shells and containing 70 cm³ of a zinc aluminate based catalyst in the form of extrudates. A settler was connected to the outlet from the fixed bed reactor to recover the crude ester, excess alcohol and glycerine.

When a certain level had been reached in the settler, the liquid phase was automatically extracted. Thus the ester and glycerine produced were collected over several days.

The methanol present in the ester was evaporated in the presence of glycerine in a "Büchi" type rotary evaporator. The glycerine was then settled out at 50° C. It was purified by a combined treatment with activated clay and activated charcoal at a temperature of 80° C. to 90° C., then filtered. Steam entrainment could then deodorise the decolorised glycerine. A crude ester remained, the composition of which is shown in Table 1 (first line).

Step 2:

This ester underwent a second operation for re-esterification of the mono-glycerides using the process described. 500 g of the crude ester obtained in the first step was introduced into a 1 liter glass flask provided with a magnetic stirrer, electrical heating and a reflux coolant with possible extraction of methanol from the head of the column, 25 g of a ground zinc aluminate equivalent to the composition of the catalyst used to produce the ester was added, and the apparatus was heated to obtain a maximum temperature of 250° C. at the bottom of the flask. Time zero was considered to be the time required to reach 250° C., namely 52 minutes. A sample was removed every hour to follow the disappearance of the mono-glycerides and the growth of the di- and tri-glycerides.

The analysis was carried out by gel permeation chromatography (GPC). At the end of the reaction, the catalyst was filtered. The results of this step are shown in Table 1 which shows that after 2 hours of reaction, there was no more mono-glyceride present in the ester.

TABLE 1

| Content (weight %) | TRI | DI | MONO | ESTERS |
|---|---|---|---|---|
| Starting product | 2.2 | 2.8 | 4 | 91 |
| T = 0 (after 52 minutes heating) | 2.8 | 3.6 | 3.3 | 90.3 |
| T = 15 min | 2.9 | 4.3 | 3.1 | 89.7 |
| T = 1 h | 3.6 | 6.7 | 2.0 | 87.7 |
| T = 2 h | 6.2 | 7.9 | — | 85.9 |
| T = 3 h | 6.5 | 6.6 | — | 86.9 |

TRI = tri-glycerides; DI = di-glycerides; MONO = mono-glycerides
ESTERS = methyl esters of rapeseed oil Step 3:

The filtrate was distilled into a glass flask by connecting the receiving flask via a very short junction followed by a condenser to prevent any reflux.

The temperature at the base of the flask was fixed at a maximum of 250° C. and the dynamic vacuum was 2 to 3 mm of mercury. A distillate was obtained which, analysed by gel permeation chromatography (GPC), showed no trace of mono-glyceride. The analysis method had a sensitivity of 0.1 to 0.2%. To verify the complete absence of mono-glycerides, a more efficient analysis was carried out which consisted of gas chromatography after silyling the sample.

Again, mono-glycerides were shown to be absent.

EXAMPLE 2

(comparative)

In order to verify the need to operate in the presence of catalysts in step 2, the crude ester obtained in 1 was heated under the conditions of Example 1 but without the catalyst. The results are shown in Table 2. It can be seen that the mono-glycerides did not disappear.

TABLE 2

| Content (weight %) | TRI | DI | MONO | ESTERS |
|---|---|---|---|---|
| Starting product | 2.2 | 2.8 | 4.0 | 91 |
| T = 0 | 2.9 | 3.9 | 3.9 | 89.3 |
| T = 1 h | 2.7 | 4.3 | 3.6 | 89.4 |
| T = 2 h | 2.9 | 5.0 | 3.4 | 88.7 |
| T = 3 h | 2.9 | 5.5 | 3.2 | 88.4 |
| T = 5 h | 3.1 | 6.5 | 2.9 | 87.5 |

EXAMPLE 3

(comparative)

The untreated crude ester was evaporated using the same system as that for Example 1. An ester was obtained which contained 1.1% by weight of mono-glycerides.

EXAMPLE 4

An acidic rapeseed oil with an acid number of 10.2, obtained by adding oleic acid to a refined rapeseed oil, was treated. 200 g of this oil was heated in the presence of 4 g of glycerine and 4 g of ground zinc aluminate. The temperature was kept at 220° C. for 5 hours in a flask analogous to that of Example 1 (step 2), except that water rather than alcohol was recovered. The mixture obtained, considered to be a neutralised oil, was used as the starting product in a process as described in Example 1, sequencing steps 1, 2 and 3. Table 3 indicates the acidity values (A. No.) obtained after this treatment.

TABLE 3

| Contents (in mg of KOH/g) | A. No. without nitrogen | A. No. with nitrogen bubbling |
|---|---|---|
| Starting product | 10.5 | 10.3 |
| T = 0 (after 40 min to reach 220° C.) | 7.4 | 4.4 |
| After 1 h at 220° C. | 3.4 | 1.7 |
| After 2 h at 220° C. | 2.6 | 1.3 |
| After 3 h at 220° C. | 2.3 | 0.9 |
| After 4 h at 220° C. | 2.3 | 0.9 |
| After 5 h at 220° C. | 2.4 | 0.9 |
| After 6 h at 220° C. | 2.04 | 0.9 |

EXAMPLE 5

A cooking oil with the following composition by weight:

<C16:0=3.2
C16:0=20.6
C16:1=1.6
C17:0=0.5
C17:1=0.4
C18:0=10.9
C18:1=39
C18:2=20.2
C18:3=0.6
>C18=0.9 was passed through a tube reactor filled with catalyst in the form of extrudates as in Example 1 (step 1) at an HSV of 1, i.e., under the same conditions as for the rapeseed oil.

The iodine number for the oil was 73.5, its acid number was low, of the order of 1.2, and the polymer content was 1.6% by weight.

After transesterification, the results for this oil were as follows:

tri-glycerides=1.4% di-glycerides=2.5% mono-glycerides=3.6% esters=92% (amounts expressed in weight %).

After step 2, the product had a mono-glyceride content of less than 0.1% but the ester content was only 86%. Flash distillation produced a compound with a purity of over 99.8%. The pour point of this ester was close to 6° C.

EXAMPLE 6

An acidic oil (containing more than 32% by weight of fatty acids) was treated with 6% of glycerine with respect to the oil, in the presence of 25% by weight with respect to the oil of the same catalyst as that used in Example 1, at a temperature of 220° C. After less than 2 hours, an oil was obtained which had an acid number of less than 1. This oil was treated in an autoclave with methanol in an alcohol/oil ratio of 1. The pressure at 230° C. was 46 bars. A product was obtained which contained more than 96% of esters and 3.1% of mono-glycerides. After filtering the catalyst, the alcohol was first evaporated by depressurising then in a rotary evaporator. The glycerine was settled out and separated. The crude ester was once again heat treated with the above catalyst but at a reduced pressure of 100 mm of mercury. After evaporating the methanol at 220° C. the catalyst was eliminated by filtering and the crude ester was flashed under reduced pressure. The distillate was free of mono-glyceride.

EXAMPLE 7

The crude ester, obtained at an HSV of 2 using a titanium catalyst obtained by the action of titanium oxide on alumina, was treated: the composition after step 1 was as follows:

tri-glycerides=11.5% di-glycerides=7.1% mono-glycerides=6.4% esters=75% (amounts expressed in weight %).

Step 2 was carried out using the same titanium catalyst at 230° C. and with 5% of catalyst, using the procedure of Example 2. Table 4 below indicates the results with and without the catalyst.

TABLE 4

| Contents | TRI | | DI | | MONO | | ESTER | |
|---|---|---|---|---|---|---|---|---|
| (wt %) | with | without | with | without | with | without | with | without |
| Starting product | 11.5 | | 7.1 | | 6.3 | | 75.1 | |
| After 15' | 12.5 | 12.5 | 8.5 | 7.9 | 4.9 | 5.9 | 74 | 73.5 |
| After 1 h | 13.4 | 12.5 | 11.1 | 8.2 | 3.05 | 5.9 | 72.2 | 73.4 |
| After 2 h | 14.4 | 13.8 | 13.2 | 8.9 | 2.0 | 5.6 | 70.1 | 71.7 |
| After 3 h | 15.0 | 11.3 | 14.5 | 8 | 1.1 | 5.45 | 69.1 | 75.2 |
| After 4 h | 16.1 | 10.5 | 16 | 8.5 | 0.2 | 5.7 | 67.5 | 75 |

Starting from a product containing 75% of methyl esters, the ester content in the final product was substantially reduced (67.5%), but in contrast the mono-glycerides disappeared almost completely.

EXAMPLE 8

25 g of commercial oleic acid was added to 500 g of a mixture of crude esters (product obtained an HSV of 0.5, with an oil/methanol volume ratio of 1 and in the presence of a zinc catalyst) with the following composition:

tri-glycerides=0.02% di-glycerides=0.10% mono-glycerides=3.90% esters=95.80%.

After heating at 200° C. for 2 hours using 2% of zinc catalyst, an ester was obtained which contained more than 92% of esters. Despite this drop in conversion, the quantity by weight of esters produced remained the same as that obtained during the first step, if this quantity was brought to 523 g of final product (the loss of weight of about 2 g corresponded to the water formed during esterification of the oleic acid).

The mono-glycerides had thus been transformed into a mixture of di-glycerides and tri-glycerides to an amount of 8%. The mono-glycerides and fatty acids were only present in trace amounts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for simultaneously producing a composition of esters of linear monocarboxylic acids containing 6 to 26 carbon atoms and glycerine with a high degree of purity, characterized in that it comprises:

a step a) in which a plant or animal oil, which may or may not be acidic, is reacted with an excess of at least one aliphatic mono-alcohol containing 1 to 4 carbon atoms, in the presence of a heterogeneous catalyst, eliminating the excess mono-alcohol and separating the glycerine, this step producing a crude ester containing fatty acid esters and residual monoglycerides and depleted of mono-alcohol;

a step b) in which the crude ester obtained undergoes transesterification or esterification of the residual monoglycerides to di- and optionally triglycerides, in the presence of a heterogeneous catalyst using the fatty acid esters or by at least one fatty acid containing 6 to 26 carbon atoms which is added; and a step c) in which the resultant ester composition from step b) is evaporated under reduced pressure to obtain an overhead ester product of said at least one aliphatic mono-alcohol of 1 to 4 carbon atom, and depleted of said mono-glycerides and an evaporation residue of di- and optionally tri-glycerides and, recycling the evaporation residue containing the di- and optionally tri-glycerides to the starting oil of step a).

2. A process according to claim 1, characterized in that:

in step a), a neutral oil is reacted with the mono-alcohol at a temperature in the range 180° C. to 250° C., at a pressure of 20 to 100 bars and in the presence of 2% to 5% by weight with respect to the oil of a heterogeneous catalyst selected from aluminates and silicates of zinc, titanium and tin, eliminating the excess mono-alcohol by evaporating and separating the glycerine by settling at a temperature of 20° C. to 100° C.;

in step b), the mono-glycerides contained in the crude ester are transformed into di- and possibly tri-glycerides, the mixture of esters obtained containing less than 0.2% of mono-glycerides, by heating at a temperature in the range 180° C. to 250° C., in the presence of a heterogeneous catalyst selected from aluminates and silicates of zinc, titanium and tin and eliminating the mono-alcohol formed during the reaction; and in step c), the ester of the mono-alcohol which is formed is evaporated at a pressure of 3 mm of mercury or less.

3. A process according to claim 1, characterized in that the catalyst is an aluminate.

4. A process according to claim 1, characterized in that the temperature of steps a) and/or b) is 180° C. to 200° C.

5. A process according to claim 1 further comprising a step d), wherein the glycerine formed in step a) is purified.

6. A process according to claim 5, characterized in that in step d), the glycerine is purified by passage over activated clay and/or activated charcoal.

7. A process according to claim 1, characterized in that a heterogeneous catalyst of the same nature is used in steps a) and b).

8. A process according to claim 1, characterized in that during step b), at least one fattty acid containing no phospholipids nor alkaline ions is added to the crude ester from step a) to transform the mono-glycerides to di- and tri-glycerides with the production of water.

9. A process according to claim 1, characterized in that the starting oil is soya oil, rapeseed oil, sunflower oil, linseed oil, peanut oil, coprah oil, palm nut oil, palm oil, safflower oil, linola oil, cottonseed oil, tallow, suet, fish oils or used cooking oil.

10. A process according to claim 1 wherein the aliphatic mono-alcohol is methanol, ethanol, secondary butanol or isobutanol.

11. A process according to claim 10, characterized in that said aliphatic mono-alcohol is methanol.

12. A process according to claim 11, characterized in that in step a), the neutral oil is reacted with methanol, at a temperature in the range 220° C. to 250° C., at a pressure of 40 to 100 bars and with a methanol/oil weight ratio of 1/3 to 2/1.

13. A process according to claim 1 wherein said oil comprises fatty acids and said process further comprises, a preliminary step for reducing the fatty acid content by reaction with small quantities of glycerine is carried out in the presence of a heterogeneous catalyst.

14. A process according to claim 13, characterized in that said heterogeneous catalyst is of the same nature as that used in step a).

15. An ester composition containing less than 0.2% by weight of mono-glycerides as produced by the process according to claim 1.

16. A process according to claim 1 wherein said oil has a combined fatty acid content including at least about 20% ($C_{16}$) saturated fatty acid by weight.

* * * * *